(12) United States Patent
Scheffler et al.

(10) Patent No.: US 8,443,634 B2
(45) Date of Patent: May 21, 2013

(54) TEXTILE-BASED ELECTRODES INCORPORATING GRADUATED PATTERNS

(75) Inventors: Kimberly Scheffler, Glen Mills, PA (US); Keith Sherrill, Huntersville, NC (US)

(73) Assignee: Textronics, Inc., Chadds Ford, PA (US)

( * ) Notice: Subject to any disclaimer, the term of this patent is extended or adjusted under 35 U.S.C. 154(b) by 219 days.

(21) Appl. No.: 12/768,340

(22) Filed: Apr. 27, 2010

(65) Prior Publication Data

US 2011/0259638 A1   Oct. 27, 2011

(51) Int. Cl.
*D04B 1/22* (2006.01)
(52) U.S. Cl.
USPC .......................................................... 66/170
(58) Field of Classification Search
USPC ............. 66/202, 171, 1, 69 R, 175–177, 173, 66/171.1; 600/390, 391, 388
See application file for complete search history.

(56) References Cited

U.S. PATENT DOCUMENTS

| | | | | | |
|---|---|---|---|---|---|
| 1,467,344 | A | * | 9/1923 | Wagstaff | 16/387 |
| 3,487,662 | A | * | 1/1970 | Safrit et al. | 66/173 |
| 3,826,246 | A | * | 7/1974 | Raddi et al. | 600/382 |
| 4,120,294 | A | * | 10/1978 | Wolfe | 600/519 |
| 4,160,711 | A | * | 7/1979 | Nishizawa et al. | 205/759 |
| 4,239,046 | A | * | 12/1980 | Ong | 600/391 |
| 4,554,923 | A | * | 11/1985 | Batters | 607/46 |
| 4,572,960 | A | * | 2/1986 | Ebneth et al. | 250/516.1 |
| 4,583,547 | A | * | 4/1986 | Granek et al. | 600/388 |
| 4,664,118 | A | * | 5/1987 | Batters | 607/46 |
| 4,809,700 | A | * | 3/1989 | Castelli | 600/384 |
| 4,911,169 | A | * | 3/1990 | Ferrari | 600/384 |
| 5,103,504 | A | * | 4/1992 | Dordevic | 2/243.1 |
| 5,275,861 | A | * | 1/1994 | Vaughn | 428/76 |
| 5,289,824 | A | * | 3/1994 | Mills et al. | 600/508 |
| 5,317,269 | A | * | 5/1994 | Mills et al. | 324/427 |
| 5,365,935 | A | * | 11/1994 | Righter et al. | 600/523 |
| 5,374,283 | A | * | 12/1994 | Flick | 607/46 |
| 5,467,773 | A | * | 11/1995 | Bergelson et al. | 600/522 |
| 5,503,887 | A | * | 4/1996 | Diaz et al. | 428/58 |
| 5,586,556 | A | * | 12/1996 | Spivey et al. | 600/510 |
| 5,771,027 | A | * | 6/1998 | Marks et al. | 343/912 |
| 5,799,333 | A | | 9/1998 | McGarry et al. | |
| 5,906,004 | A | * | 5/1999 | Lebby et al. | 2/1 |

(Continued)

FOREIGN PATENT DOCUMENTS

| | | |
|---|---|---|
| CA | 2428884 | 5/2002 |
| EP | 1 319 741 A1 | 6/2003 |

(Continued)

OTHER PUBLICATIONS

G. Troster, "The Agenda of Wearable Healthcare," IMIA Yearbook of Medical Informatics 2005: Ubiquitons Health Care Systems, Hauz R., Kulikouskim C., eds. Stuttgart 2004 pp. 125-138.

(Continued)

*Primary Examiner* — Danny Worrell
(74) *Attorney, Agent, or Firm* — Novak Druce Connolly Bove + Quigg LLP

(57) ABSTRACT

Textile-based electrodes incorporating graduated patterns include a fabric portion having non-conductive yarns and an electrically conductive region having electrically conductive yarn filaments. The electrodes can further include float yarns and can be configured in a textured or ribbed construction. When incorporated into a garment, the electrodes can be used to monitor biophysical characteristics, such as the garment wearer's heart rate.

23 Claims, 20 Drawing Sheets

U.S. PATENT DOCUMENTS

| | | | | |
|---|---|---|---|---|
| 5,968,854 | A * | 10/1999 | Akopian et al. | 442/132 |
| 6,047,203 | A * | 4/2000 | Sackner et al. | 600/388 |
| 6,066,093 | A * | 5/2000 | Kelly et al. | 600/386 |
| 6,145,551 | A * | 11/2000 | Jayaraman et al. | 139/387 R |
| 6,210,771 | B1 * | 4/2001 | Post et al. | 428/100 |
| 6,341,504 | B1 * | 1/2002 | Istook | 66/172 E |
| 6,356,238 | B1 * | 3/2002 | Gainor et al. | 343/718 |
| 6,377,216 | B1 * | 4/2002 | Cheadle et al. | 343/700 MS |
| 6,381,482 | B1 * | 4/2002 | Jayaraman et al. | 600/388 |
| 6,399,879 | B1 * | 6/2002 | Ueda et al. | 174/389 |
| 6,496,721 | B1 * | 12/2002 | Yonce | 600/509 |
| 6,677,917 | B2 * | 1/2004 | Van Heerden et al. | 343/897 |
| 6,680,707 | B2 * | 1/2004 | Allen et al. | 343/718 |
| 6,736,759 | B1 * | 5/2004 | Stubbs et al. | 482/8 |
| 6,738,265 | B1 * | 5/2004 | Svarfvar et al. | 361/818 |
| 6,748,260 | B2 * | 6/2004 | Au et al. | 600/509 |
| D492,999 | S * | 7/2004 | Lax | D24/167 |
| 6,788,978 | B2 * | 9/2004 | Vesnaver | 607/115 |
| 6,854,296 | B1 * | 2/2005 | Miller, III | 66/190 |
| 6,941,775 | B2 * | 9/2005 | Sharma | 66/202 |
| 6,970,731 | B1 * | 11/2005 | Jayaraman et al. | 600/388 |
| 7,308,294 | B2 | 12/2007 | Hassonjee et al. | |
| 7,474,910 | B2 | 1/2009 | Hassonjee et al. | |
| 7,559,902 | B2 * | 7/2009 | Ting et al. | 600/529 |
| 8,082,762 | B2 * | 12/2011 | Burr | 66/175 |
| 8,116,898 | B2 * | 2/2012 | Chung et al. | 700/141 |
| 2003/0224681 | A1 * | 12/2003 | Koch | 442/131 |
| 2004/0023576 | A1 * | 2/2004 | Rock et al. | 442/59 |
| 2004/0171284 | A1 | 9/2004 | Sweetland et al. | |
| 2004/0215089 | A1 * | 10/2004 | Bergelson et al. | 600/510 |
| 2004/0235381 | A1 * | 11/2004 | Iwasaki et al. | 442/190 |
| 2005/0034485 | A1 * | 2/2005 | Klefstad-Sillonville et al. | 66/171 |
| 2006/0117805 | A1 * | 6/2006 | Valentine et al. | 66/171 |
| 2006/0183990 | A1 * | 8/2006 | Tolvanen | 600/386 |
| 2007/0106343 | A1 | 5/2007 | Monogue et al. | |

FOREIGN PATENT DOCUMENTS

| | | |
|---|---|---|
| FR | 2 745 690 A1 | 9/1997 |
| GB | 2 116 725 A | 9/1983 |
| WO | WO-92/13352 A1 | 8/1992 |
| WO | WO-01/02052 A2 | 1/2001 |
| WO | WO-01/37366 A1 | 5/2001 |
| WO | WO-01/39326 A1 | 5/2001 |
| WO | WO-02/071935 A1 | 9/2002 |
| WO | WO-03/094717 A1 | 11/2003 |
| WO | WO-2004/006700 A1 | 1/2004 |
| WO | WO-2004/058346 A1 | 7/2004 |
| WO | WO-2004/097089 A1 | 11/2004 |
| WO | WO-2004/100784 A2 | 11/2004 |
| WO | WO2004098703 | 11/2004 |
| WO | WO-2004100784 A2 | 11/2004 |
| WO | WO-2005032366 | 4/2005 |

OTHER PUBLICATIONS

A.M. Albisser, et al., "Atraumatic electrodes for cardiac monitoring," Journal of Association for the Advancement of Medical Instrumentation, vol. 5, No. 2, Apr. 1971.

Carla Hertleer, et al., "Intelligent Textiles for Children in a Hospital Environment," 2nd Autex Conference, Jul. 2002, pp. 44-48.

Scilingo E.P., et al., "Performance Evaluation of Sensing Fabrics for Monitoring Physiological and Biomechanical Variables," IEEE Transcations on Information Technology in Biomedicine, vol. 9, No. 3, Sep. 2005, pp. 345-352.

Krzysztof Gniotek, et al., "The Basic Problems of Textronics," Fibres & Textiles, Jan./Mar. 2004, vol. 12, No. 1 (45), pp. 13-16.

Wijesiriwardana et al., "Fiber-Meshed Trasducers Based Real Time Wearable Physiological Information Monitoring System" Processing of the Eighth International Symposium on Werable Computers (ISCW 2004).

* cited by examiner

TEXTILE-BASED ELECTRODES INCORPORATING GRADUATED PATTERNS

FIELD OF THE INVENTION

The invention relates to a textile-based electrode or textile-based electrode system, wherein the textile-based electrode incorporates graduated patterns. The peripheries of the patterns may be curvilinear, rectilinear, or mixtilinear. The textile-based electrode or textile-based electrode system is integrated into a wearable article. The wearable article can be, for example, adapted for biophysiological monitoring using textile-based electrodes to receive biophysiological signals from the wearer.

BACKGROUND OF THE INVENTION

Textile-based electrodes consisting of electrically conductive wires or electrically conductive yarns with metal fibers surrounded by a region of electrically nonconductive textile fibers can be integrated with a wearable article, such as a garment. The wires or electrically conductive yarns with metal fibers are incorporated into the wearable article. The wearable article is then adapted to receive or transmit electrical impulses to or from the wearer and, in turn, to or from an electrical device. The patent document WO 01/02052, assigned to Bekaert, discloses such a wearable article.

Wearable textile-based sensors made from yarns with metal fibers for sensing or otherwise reporting the heart rate (the pulse) of the wearer are disclosed in patent document WO 02/071935, assigned to RTO Holding OY.

Patent document WO 03/094717, assigned to Koninklijke Philips Electronics NV, discloses a textile article that is provided with a region of skin contacting electrodes that are fully integrated within a textile article. The disclosed textile article takes the form of a "bra or a ladies top," which is otherwise electrically nonconducting. The article is provided with partially overlapping layers of electrically conductive material, which may be made from metal fibers, and electrically insulative material arranged to partially cover and electrically isolate the electrically conductive material.

Patent document WO 2004/006700, assigned to Tefron Ltd., discloses a circularly knit garment having an inner surface electrically-conductive region, which can be metallic, disposed close to the wearer's skin. The inner electrically-conductive region cooperates to conduct electrical signals to an outerlying electrically-conductive region. Such electrical signals may include the heart rate coming from the wearer or an electro-stimulation means going to the wearer.

Each of these patent documents relates an objective to provide an electrically-conductive region, which can comprise metallic wires or fibers, and which can function as an electrode integrated with a garment, a belt, or other wearable article of traditional textile construction. Generally, these patent documents disclose an electrically-conductive region that is otherwise electrically isolated from the remainder of the garment or wearable. These regions may be knitted into the garment. Furthermore, these patent documents disclose placing at least one electrically-conductive region of the garment in close contact with the skin of the wearer. As a result, the electrode, formed by this electrically conductive region in contact with the skin, provides a pick-up point for electrical signals generated within the corpus of the wearer. Alternatively, such an electrode provides a point of contact on the skin to receive an electrical signal generated externally to the wearer. In summary, these patent documents provide means to communicate electrical signals to or from the corpus of a garment wearer.

In addition, these patent documents generally disclose at least a second textile electrode. More often, the second electrode is integrated with the garment and located at or near an exterior surface of the garment. The second electrode can also be advantageously placed overlying the electrode in skin contact, while also having a portion of the garment's electrically insulating materials of construction therebetween. Where an electrical connection between the electrode(s) in skin contact and the exterior electrode(s) is desired, such connection can be established using metallic wires. Alternatively, the skin contact electrode can be folded over in such a manner as to form the exterior surface electrode continuously.

U.S. Pat. Nos. 7,308,294 and 7,474,910 assigned to Textronics Inc. show other wearable textile-based sensors for monitoring biophysiological signals.

Where an electrical connection between a garment-integrated electrode in skin contact with the wearer and a garment-integrated exterior electrode is established using metallic wires or yarns with metal fibers, certain limitations may exist. Such limitations can result during the knitting process because of the nature of the tools used. For example, needle wear and breakage can occur due to metal-to-metal contact between the needle and the metallic wires or yarns with metal fibers. To increase the efficiency and productivity of knitting machines, an increase in operating speed is also desired. Such an increase, however, can also result in increased needle wear. Depending on the type of yarns selected, wear can also be attributed to contaminants within the yarns, affecting not only needles but also the yarn carriers, sinkers, and cams.

For example, for high speed knitting on circular knitting machines, needles are frequently replaced due to the repetitive contact between metallic wires or yarns with metal fibers and the metallic needles used during manufacture of the wearable. Needle wear can result from the free end of the latch engaging the hook of the needle when the latch swings to the closed position during the movement of the needle to a lowered stitch loop forming position. Wear of the needle can also occur when the latch swings to the fully open position as the needle is raised to clear the stitch loop below the latch. The impact of the latch against the needle can also cause metal fatigue and latch failure, in some cases.

Needle wear can also result due to the properties of the yarns used. For example, yarns made from metal coated fibers are rigid and have very little "give," resulting in wear on the knitting elements. This especially occurs when the metal coated fiber is first pulled into the knitted structure. Wear also can occur when spun yarns are made from natural or chemical fibers used during manufacture of the wearable article. Some chemical fibers may, for example, have matting agents that generate needle wear. In addition, spun yarns made from natural fibers may contain foreign particles due to how the fibers are cultivated, harvested, and the cleaning methods used after harvesting. A frequent contaminant in these types of yarns is silica. These impurities in the yarns can abrade needles. The consequences of needle wear include needle lines, unintended holes in the fabric, unintended tuck stitches, unintended double stitches, yarn breakage, machine stops and downtime. These consequences result in defective products and increase the time for manufacture and the cost of wearable articles that incorporate textile-based electrodes.

Other limitations can also be present, for example, when biophysical monitoring via electrical contact with the corpus is desired. These limitations may include the difficulty of making metallic wires or yarns with metallic fibers part of a traditionally fabricated textile due to the fragility and durable flexibility of metal wires and yarns with metal fibers.

Other configurations may also suffer certain limitations. For example, configurations incorporating "folded over" and partially overlapping layers of electrically conductive material (with electrically insulative material arranged to electrically isolate the electrically conductive material) may severely limit the freedom to design the placement of electrodes integrated with a garment or textile article.

Accordingly, there exists a need to provide a textile-based electrode capable of overcoming one or more of the deficiencies of the prior art.

SUMMARY OF THE INVENTION

The present invention, in one aspect, provides a textile-based electrode with at least one graduated pattern. In a second aspect, the present invention provides an electrode system that incorporates textile-based electrodes with graduated patterns into a wearable article, such as a garment. These textile-based electrodes can include a fabric portion having stretch-recovery non-conductive yarns and an electrically conductive region having stretch-recovery electrically conductive yarn filaments.

The textile-based electrode system can include first and second fabric portions that include electrically conductive regions. The electrically conductive regions may be disposed in a partially overlapping relationship, allowing for a region of partial physical contact that can result in electrical conduction between the electrically conductive regions.

At least one of the electrically conductive regions can include a float yarn. In addition, at least one of the electrically conductive regions can be made with an elastified electrically conductive yarn and/or an elastic yarn at least partially plated with a conductive yarn. In one embodiment, the electrically conductive regions can include a fabric having a textured or ribbed construction. In further embodiments, the electrically conductive regions can include a portion or portions having at least one hydrophobic material and/or can be separated by a region having at least one hydrophobic material.

The selected pattern for the electrically conductive regions can impact the manufacture of the textile based electrodes. In particular, it has been found that graduated patterns lessen needle wear, needle breakage, and needle misalignment. By "graduated pattern" herein is meant a textile based electrode that has at least one graduated end that changes gradually or by degrees, such as, for example, patterns with rounded, angled, curved, or staggered ends. In particular, using graduated patterns places less stress on needles compared to patterns with straight ends. For example, when knitting rectangular or square patterned regions with straight ends, knitting machines begin and end using the same needle. The continued stress on a single needle may cause needle misalignment such that over-knitting and mis-plating occurs, resulting in irregularly shaped sensor regions and other defects. In comparison, when knitting graduated pattern regions, knitting machines begin and end using different needles on each course. Thus, needle stress is distributed among several needles. In addition, other components of the knitting machine benefit from the use of patterns having graduated ends, including, but not limited to yarn cutting blades. The use of graduated patterns thus reduces defects, allows for more even distribution of stress on needles, cutting blades and other components. As such, using graduated patterns, the manufacture of the textile based electrodes is improved, resulting in faster knitting speeds, and longer life of knitting machine components, among other improvements.

Textile-based electrodes falling within the scope of the present invention can be connected to a measuring device. The measuring device can, for example, be used to monitor biophysical signals of a wearer of a garment incorporating the electrodes. For instance, in one embodiment, the textile-based electrodes can be used to facilitate monitoring a wearer's heart rate.

BRIEF DESCRIPTIONS OF THE DRAWINGS

Embodiments of the present invention will be described in the following detailed description with reference to the following drawings.

DETAILED DESCRIPTION OF THE INVENTION

Figure 1A:
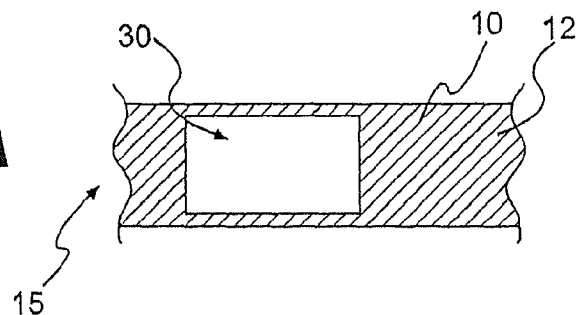
FIGS. 1A and 1B are schematic representations of a top plan view and a bottom plan view of a first textile-based electrode.

The present invention, in one embodiment, can provide a textile-based electrode capable of being fully integrated with a wearable article that can be adapted to allow contact of the electrode with the corpus of the wearer. The textile-based electrode can incorporate graduated patterns to lessen needle wear, needle breakage, and needle misalignment, among other improvements. The textile-based electrode disclosed herein is also capable of being adapted for the transmission of electrical signals to the wearer of an article integrated with the electrode. For example, such a textile-based electrode may be adapted for the biophysiological monitoring of the wearer.

The textile-based electrode disclosed herein is also capable of transmitting or receiving electrical signals via contact with the corpus of the wearer without relying on fragile connection wires. The textile-based electrode may also be specifically adapted for the reliable contact with corpus of the wearer, further providing relatively consistent electrical continuity with a complementary textile-based electrode (i.e., without signal loss or short circuiting while the wearer moves freely). In this regard, the textile-based electrode may be stretchable in the electrically conductive area due to the presence of elastic materials that are knitted or woven with electrically conductive yarns or filaments and/or through the use of yarns or filaments that are both elastic and electrically conductive.

In one embodiment, the textile-based electrode can be included within an electrode system comprising a first fabric portion provided with a portion of electrically conductive yarns in a knit construction. The knit construction can, for example, be chosen from among single jersey, ribbed knit, mock ribbed knit, and ribbed knit 1×1 and 1×3 constructions. The portion of electrically conductive yarns can be surrounded by, and electrically isolated from, the first fabric portion.

In other embodiments, the textile-based electrode can have a graduated pattern. In particular, the end portions of the textile-based electrode can be rounded, angled, curved, or staggered. In these embodiments, the textile-based electrode can also be elongated with one or more rounded, curved, slanted or angled ends, or more compact with a staggered, rounded, curved, slanted or angled periphery.

The textile-based electrode can exhibit stretchability in the electrically conductive area due to the presence of a material, such as Lycra® spandex, plated with a conductive yarn or filament. By "plated" is meant herein a yarn covered by another yarn. The textile-based electrode can also exhibit stretchability in the electrically conductive area through the use of a conductive yarn, such as the conductive yarns disclosed in WO 2004/097089A1 or U.S. Pat. No. 7,135,227 (assigned INVISTA Technologies S.à.r.l.), the entire disclosure of which is incorporated herein by reference. In addition, the textile-based electrode can exhibit stretchability by using different types of knit constructions, such as a ribbed construction (including, for example, 1×1 or 1×3 ribbed knit constructions).

In a further embodiment, a textile-based electrode is provided within an electrode system, which comprises at least a first fabric portion and a second fabric portion disposed in a partially overlying relationship. The first fabric portion may comprise at least a first electrically conductive region (a first "electrode") and the second fabric portion may comprise at least a second electrically conductive region (a second "electrode"). The electrically conductive region of the first fabric portion and the electrically conductive region of the second fabric portion can cooperate to provide a region of partial physical contact. This physical contact region can thereby establish electrical conduction between the first and second "electrodes."

The first and second electrically conductive regions or "electrodes" each comprise at least a portion of electrically conductive yarns. In addition, the first and second electrically conductive regions or "electrodes" may each further comprise at least a portion of "float yarns."

Embodiments falling within the scope of the present invention may be further described with reference to the figures disclosed herein.

Figure 1B:
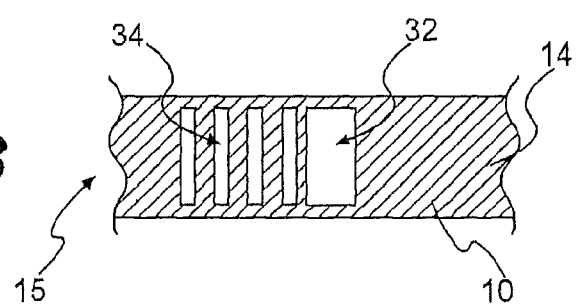

In one embodiment, a first textile-based electrode is provided within an electrode system comprising a first fabric portion 10 that is provided with a portion of electrically conductive yarn 30, as represented in FIGS. 1A and 1B. In this embodiment, the portion of electrically conductive yarn 30 (FIG. 1A) is surrounded by and electrically isolated from the first fabric portion 10.

Figure 1C:
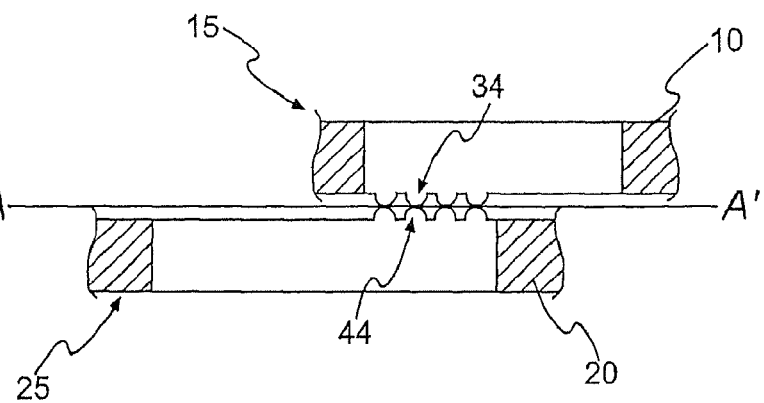
FIG. 1C is a schematic representation in side elevation of the first textile-based electrode of FIGS. 1A and 1B, comprising a portion of electrically conductive float yarns in contact with a portion of electrically conductive float yarns of a second textile-based electrode of FIGS. 1D and 1E.
Figure 1D:
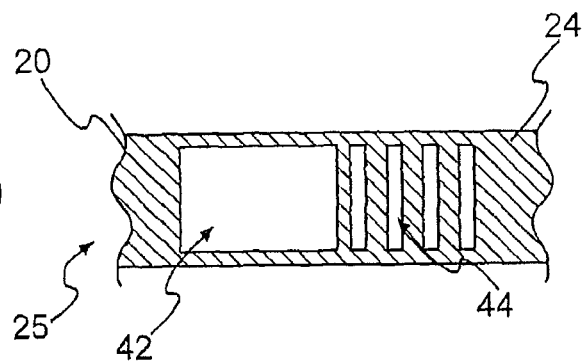
FIGS. 1D and 1E are schematic representations of a top plan view and a bottom plan view of a second textile-based electrode.
Figure 1E:
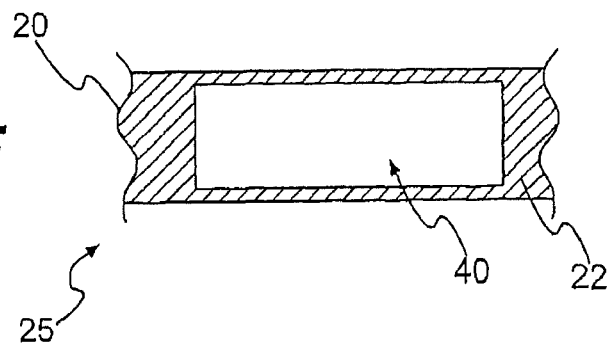

A second textile-based electrode comprises a first fabric portion 20 that is provided with a portion of electrically conductive yarns 40, as represented in FIGS. 1D and 1E.

In embodiments falling within the scope of the invention, a knit construction can be used. The knit construction may, for example, be chosen from among single jersey, mock ribbed knit, and ribbed knit 1×1 and 1×3 constructions for both the fabric portion 10 and 20 and the conductive yarns 30 and 40. As is known to a person having skill in the art, in such knit fabrics, the wales, or vertical rows of stitches, typically intermesh alternately on the face (odd number wales) and on the back (even number wales) of the fabric. Rib-knit fabrics of this type have been shown to have good elasticity in the length and width directions and can provide good body form fitting garments.

A further embodiment of the invention provides for the conductive yarns 30 and 40 to be knitted in with floats. Floats, as known to a person having skill in the art, comprise a portion of yarn that extends over the fabric without being knitted in (i.e. floating or lying on the fabric surface). Fabric portions 10 and 20 with electrically conductive yarns 30 and 40 in a rib-knit construction can provide a textile-electrode structure wherein yarns 30 and 40 are floated over the ribbed structure of the fabric. As a result, these conductive float yarns 34 and 44 (FIGS. 1A, 1B, 1D, and 1E) are readily accessible on the surface of the fabric. The ready accessibility of the conductive float yarns 34 and 44 facilitates electrical contact between the conductive yarn portions of fabric through the physical contact of the float yarns. In one embodiment, the electrical contact between conductive yarn portions may be further facilitated by stitching conductive float yarns 34 and 44 together.

As shown in FIG. 1C, the first textile-based electrode 15 and the second textile-based electrode 25 may be placed adjacent to one another, putting float yarns 34 and 44 in contact with one another to establish electrical conductive contact.

Materials suitable for use as conductive yarns 30 and 40, and thus the float yarns 34 and 44, include, for example, those yarns disclosed in patent document WO 2004/097089A1 or U.S. Pat. No. 7,135,227 (assigned to INVISTA Technologies S.à.r.l.), the entire disclosure of which is incorporated herein by reference. The conductive yarns disclosed within WO 2004/097089A1 or U.S. Pat. No. 7,135,227 (hereinafter called ETG1 yarns) can inherently provide elastic stretch and recovery and can lend themselves to knit constructions for embodiments disclosed herein. Inelastic conductive filaments, suitable for preparing the elastic conductive yarns according to the disclosures in WO 2004/097089A, include those yarns from BEKAERT Fibre Technologies (such as CONDUFIL® 80 dtex and 24 filament yarns) and those yarns known as Xstatic® yarns of a silver metallized nylon yarn from Laird Sauquoit Industries (Scranton, Pa., USA 18505).

Electrically nonconductive yarns or traditional textile yarns can be advantageously employed for the bulk of the fabric portion. These yarns can include, for example, cotton, cellulosics, silk, ramie, polyester, and/or nylon. The bulk of the fabric portion can also include combinations of polyester and nylon with elastic yarns (such as LYCRA® branded spandex from INVISTA™ S.à.r.l.).

Figure 1F:
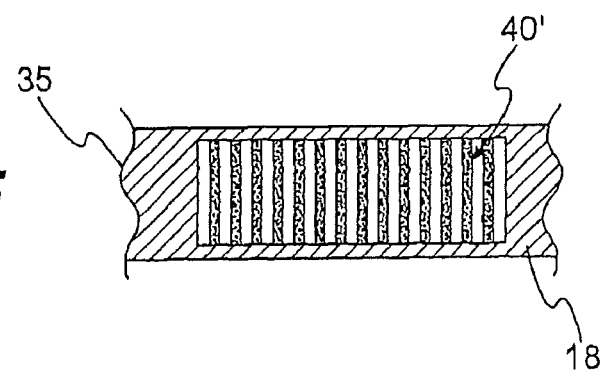
FIG. 1F is a schematic representation of an integrated textile electrode comprising a portion of electrically conductive region using different types of knit construction.

In this regard, FIG. 1F shows a representation of an integrated textile electrode 35 having a portion of an electrically conductive region 40' using different types of knit construction, including a ribbed construction (i.e. 1×1 or 1×3 rib). Such electrode can be within a larger region 18 surrounding the electrically conductive region 40' and having, for example, a ribbed construction. The electrode area can stretch due to, for example, the presence of Lycra® spandex plated with the conductive yarns, or through the use of an elastic conductive yarn, such as a yarn disclosed in WO 2004/097089A1 (ETG1). In addition, through the use of a ribbed construction and elastic materials, the stretch electrode can provide improved contact with the skin and hence better signal pick-up.

Such ribbed construction stretch electrodes can be made, for example, on SM8-TOP1, SM8-TOP2, and SM4-TR2 knitting machines from SANTONI (from GRUPPO LONATI, Italy), using 13", 14", 15", 17" and 20" cylinders.

Examples of conductive yarns that can be used in such integrated textile electrodes include Xstatic® 70 denier 2 ply (e.g. silver metallized nylon yarn of 70 denier and 34 filaments from Laird Sauquoit Industries (Scranton, Pa., USA 18505) and ETG1 yarns (hollow spindle double covered 70 denier nylon yarn on LYCRA® Type 162 "clear" and 20 micron silver-plated copper wire from Elektro Feindraht).

FIG. 1C shows an edgewise view of fabric portion 10 and fabric portion 20 oriented about the axis extending from A to A'. As shown in this figure, physical contact can occur between yarn floats 34 in fabric 10 and yarn floats 44 in fabric 20. This physical contact of floats 34 and 44, or a plurality of similar floats, can provide electrical continuity between the fabric portions 10 and 20.

As represented in FIG. 1C, when the conductive float yarn portion 34 of fabric portion 10 is in contact with the conductive float yarn portion 44 of fabric portion 20, the conduction of an electrical signal between the two conductive yarn portions, i.e. from conductive portion 30 on surface 12 to conductive portion 40 on surface 22, can be enabled.

Figure 2A:
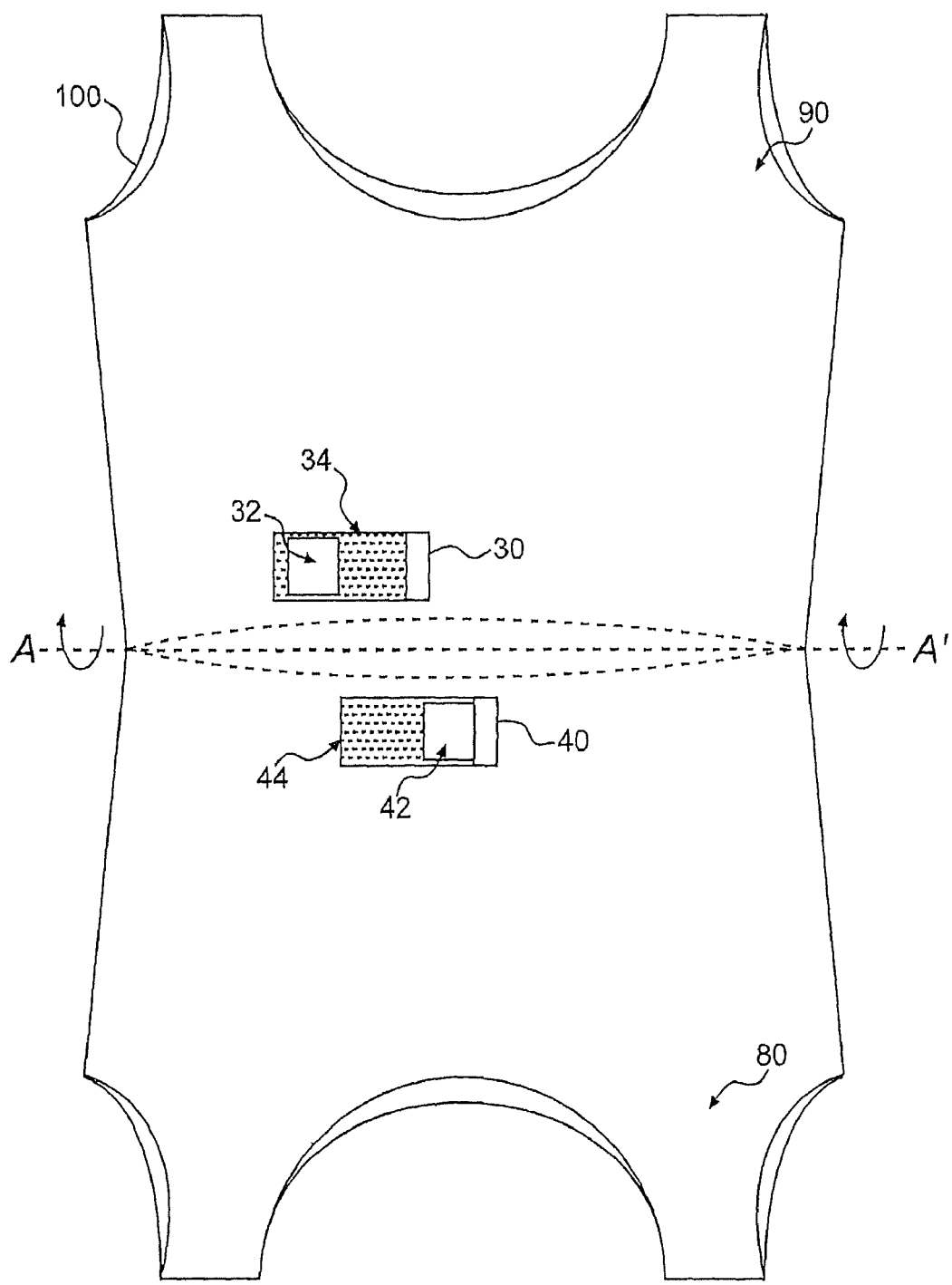
FIGS. 2A and 2B are schematic representations of an upper body wearable article having textile-based electrodes.
Figure 2B:
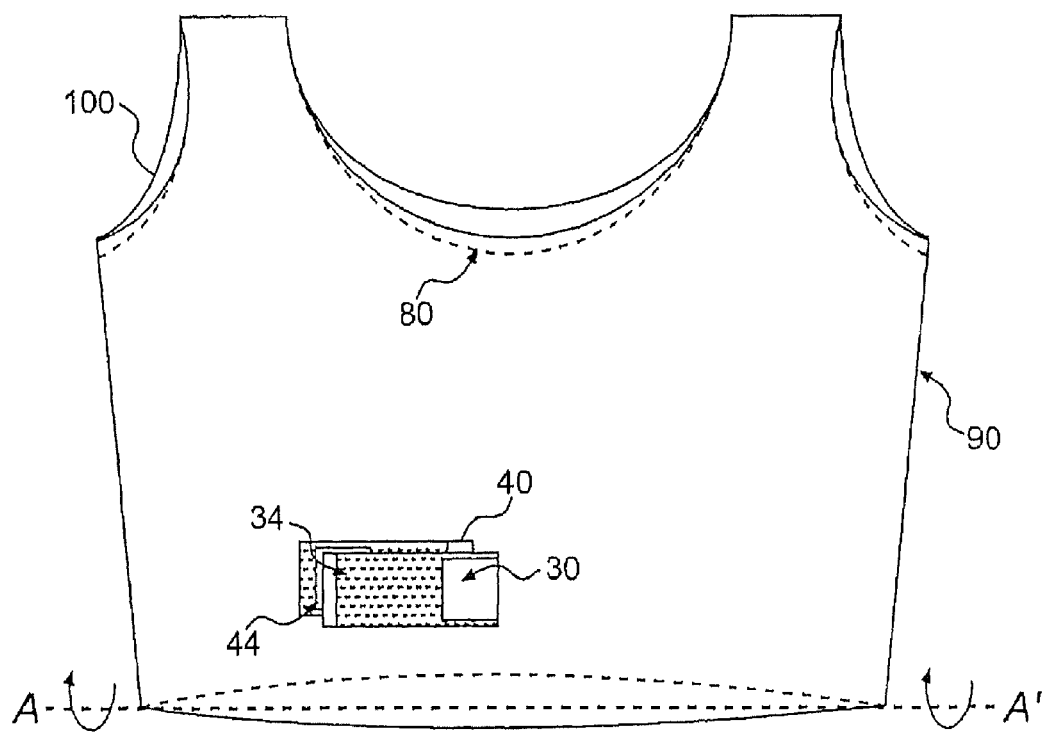

An embodiment of a textile-based electrode system, fully integrated with a wearable article, such as a shirt, is represented with the aid of FIGS. 2A and 2B. In these figures, a wearable 100 is represented as an upper body worn garment. The wearable 100 can be constructed using commonly practiced seamless (circular) knitting technology. In an "as-knitted" form using, for example, seamless technology, wearable 100 takes the shape of a tube with upper 90 and lower 80 mirror image portions about axis-AA'. The lower portion 80 in FIG. 2A, may be folded into the upper portion 90, to form a two ply garment having inner and outer portions, as represented in FIG. 2B. A waist band of a garment can be constructed in a similar manner.

FIGS. 2A and 2B represent wearable 100 as having a textile-based electrode system fully integrated with it. The outer surface portion of the textile-based electrode system 40, is shown as being associated with lower portion 80. The outer surface portion of the textile-based electrode system 40 is electrically continuous with inner surface portions 42 and with float yarns 44, shown with dashed lines. The outer surface portion of the textile-based electrode system 30 is shown as being associated with upper portion 90 and is electrically continuous with inner surface portions 32 and with float yarns 34, shown with dashed lines. When lower portion 80 is folded into upper portion 90 of wearable 100, float yarn portions 34 and 44 come into physical contact, as shown in FIG. 2B (in the manner as represented by FIG. 1C). As a result of the physical contact between portions 34 and 44, an electrical signal can pass in either direction from electrode 30 on the outer surface of the two ply garment 100, to electrode 40 on the inner surface and thereon to the skin of the wearer.

Figure 3A:
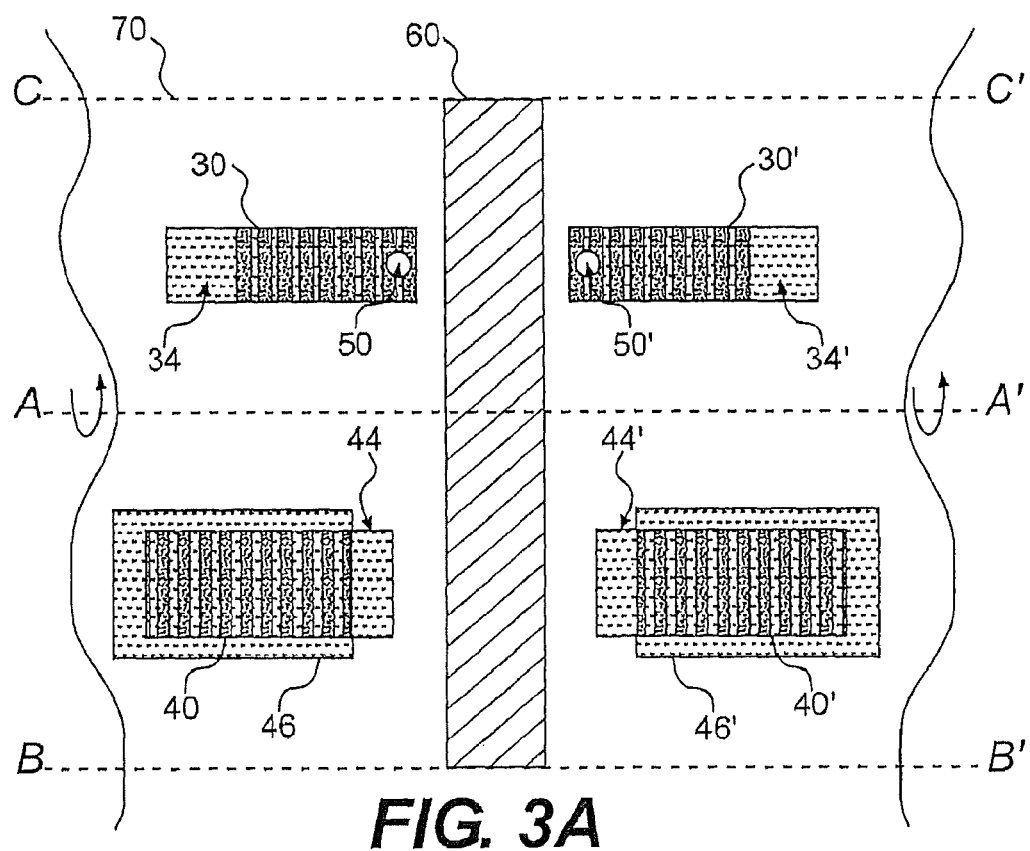
FIG. 3A is a schematic representation in front plain view of textile-based electrodes.
Figure 3B:
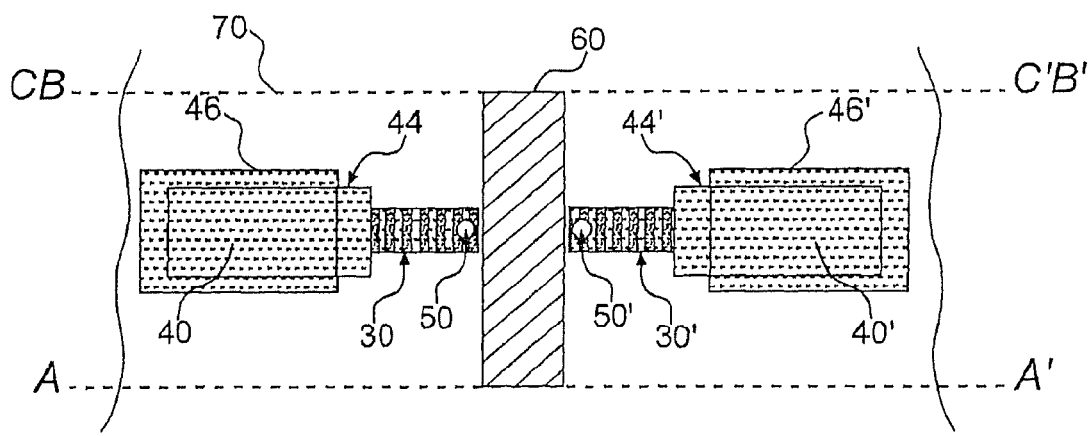
FIGS. 3B and 3C are schematic representations of the textile-based electrodes in a folded configuration.

Another embodiment of a textile-based electrode system is represented with the aid of FIGS. 3A and 3B. In FIG. 3A a portion of a fabric 70, bounded by two horizontal axes, CC' and BB', is represented. A third horizontal axis, AA', placed equidistant in a vertical direction from both CC' and BB', is also represented in FIG. 3A.

In FIGS. 3A and 3B, two textile-based electrodes are placed opposite one another in the horizontal direction. These electrodes include first and second outer portions of conductive yarns 30 and 30', as represented in FIG. 3A. These electrodes further include inner conductive yarn portions 34 and 34', represented in FIG. 3A, using dashed lines to illustrate the float yarns lying directly under yarn portions 30 and 30' respectively.

Similarly, FIG. 3A shows components of textile-based electrode systems, including third and fourth outer portions of optional moisture retentive yarns, such as cotton, 46 and 46'. Such electrode systems further include inner conductive yarn portions 44 and 44', represented in FIG. 3A using dashed lines to illustrate the float yarns lying directly under conductive yarn portions 40 and 40' respectively. Conductive yarns 40 and 40', are respectively continuous with 44 and 44', and surrounded by optional moisture retentive yarn portions 46 and 46', respectively.

Further represented in FIG. 3A, is a metallic connector 50 adapted to function as a central point for electrical connection to a textile-based electrode.

FIG. 3B is a representation of fabric portion 70 after folding along horizontal axis AA' and causing axes CC' and BB' to meet co-linearly along a new horizontal axis CB-C'B'. As a result of making this fold in fabric portion 70 along horizontal axis AA', a two-ply fabric portion is formed. The inner conductive yarn portions and the associated float yarn portions, respectively 34 and 44 and 34' and 44', are brought into physical contact (as represented in FIG. 3C) on an inner portion of the two-ply fabric portion.

Figure 3C:
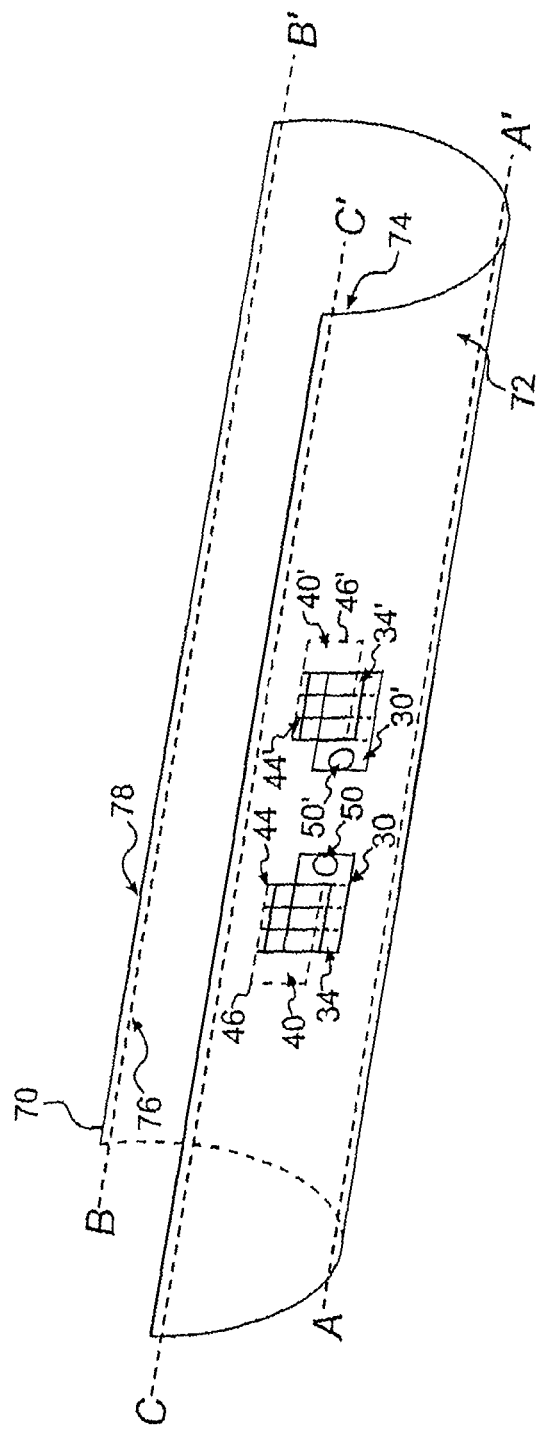

As represented by FIG. 3C, the conductive yarn portions 30 and 30' are on an outer surface portion 72 and the conductive float yarn portions 34 and 34' are on an inner surface portion 74 of the two-ply fabric. Similarly, as represented by FIG. 3C, the optional moisture retentive yarn portions 46 and 46' are on an outer surface portion 78 of the two-ply fabric. The conductive yarn portions 40 and 40' are on outer surface portion 78 and float yarn portions 44 and 44' are all on an inner surface portion 76 of the two-ply fabric, as represented by FIG. 3C.

Referring now to FIG. 3C, the folded over fabric portion 70 is represented as having surface portions 78 and 72, as well as two textile-based electrodes, which are electrically continuous from surface portion 78 to surface portion 72. Such arrangement allows for the transmission and reception of electrical signals between surface portions 72 and 78. Connection points 50 and 50' can be adapted for sending or receiving such electrical signals.

Figure 4:
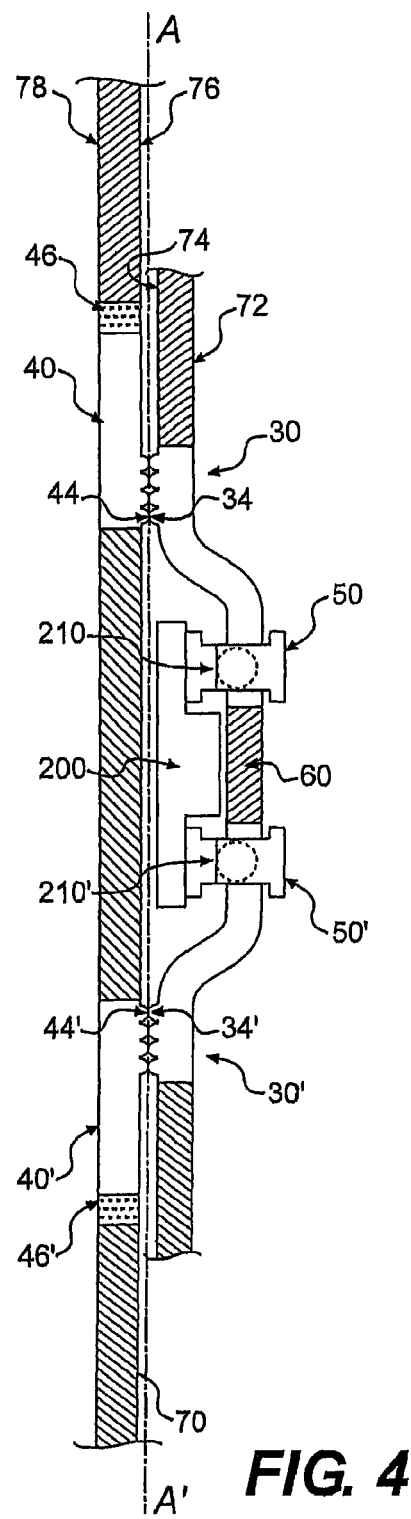
FIG. 4 is a schematic representation in partial cross-section of a pair of textile-based electrodes adapted to communicate with electronics capable of biophysical monitoring.

A means for adapting 50 and 50' for receiving and sending electrical signals is represented with the aid of FIG. 4. In this figure, fabric portion 70 is represented from a view between surfaces 74 and 76, which are facing one another as a result of folding 70 about horizontal axis AA' (as shown in FIG. 3B). Surface 78 (the side adapted to be in contact with a wearer's skin) contains conductive yarn portions 40 and 40' and surface 72 contains conductive yarn portions 30 and 30'. Between surfaces 76 and 74, conductive float yarn portions 44 and 44' are brought into physical contact with conductive float yarn portions 34 and 34', thereby providing electrical continuity between conductive yarn portions 40 and 40' and conductive yarn portions 30 and 30'.

Electrically conductive contacts 50 and 50' are respectively attached to conductive yarn portions 30 and 30'. Electrically conductive contacts 50 and 50' may be made of any electrically conductive material, such as, for example, metallic conductors. Electrically conductive contacts 50 and 50' can be attached to conductive yarn portions 30 and 30' such that they communicate through 30 and 30' and are capable of contacting or engaging with electrically conductive contacts 210 and 210' respectively. Electrically conductive contacts 210 and 210' are associated with 200, an electrical device.

Electrical device 200 is represented in FIG. 4 as being placed between surfaces 74 and 76 of the folded over fabric portion 70. As a result, an electrical signal originating at conductive yarn portions 40 and 40' can be conducted directly to electrically conductive contacts 210 and 210' (as well as to 30 and 30'), respectively, which are each associated with electrical device 200. Alternatively, an electrical signal originating with electrical device 200 may be conducted directly to electrically conductive contacts 210 and 210' (as well as to 30 and 30'), and thereon to conductive yarn portions 40 and 40'.

An embodiment including optional yarns 60 is shown in FIG. 4, where the optional yarns 60 include, for example, PTFE filaments. The use of optional filaments 60 reduces the possibility of short circuiting of the textile-based electrodes in garments expected to be worn by heavily perspiring wearers. In one embodiment, the PTFE filaments can be wrapped about or twisted with LYCRA® brand spandex yarns. Otherwise, these yarns need no special preparation and can be readily integrated with the traditional textile filaments of the garment construction.

Figure 5:
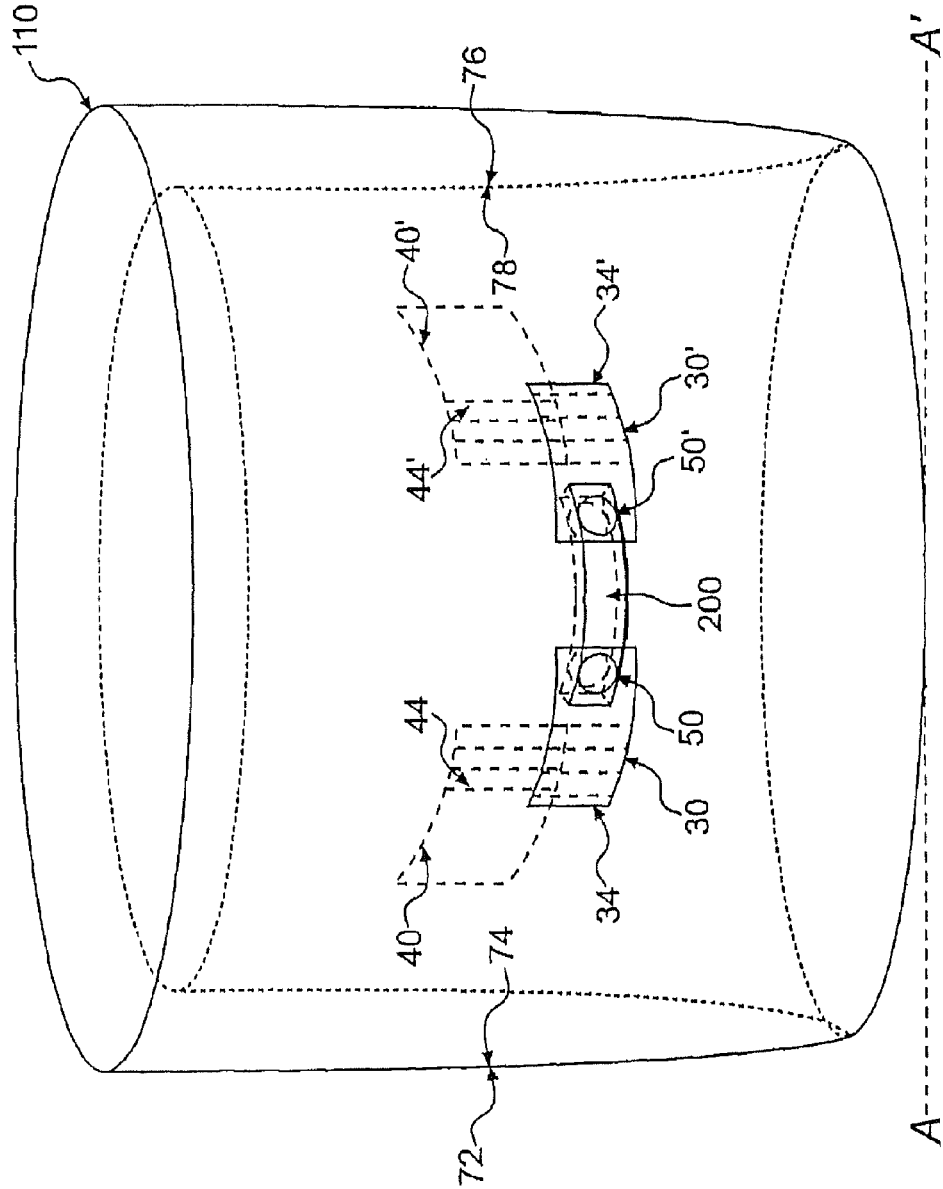
FIG. 5 is schematic representation of a continuous band adapted to wearing about the body and adapted for use with electronics capable of biophysical monitoring.
Figure 6:
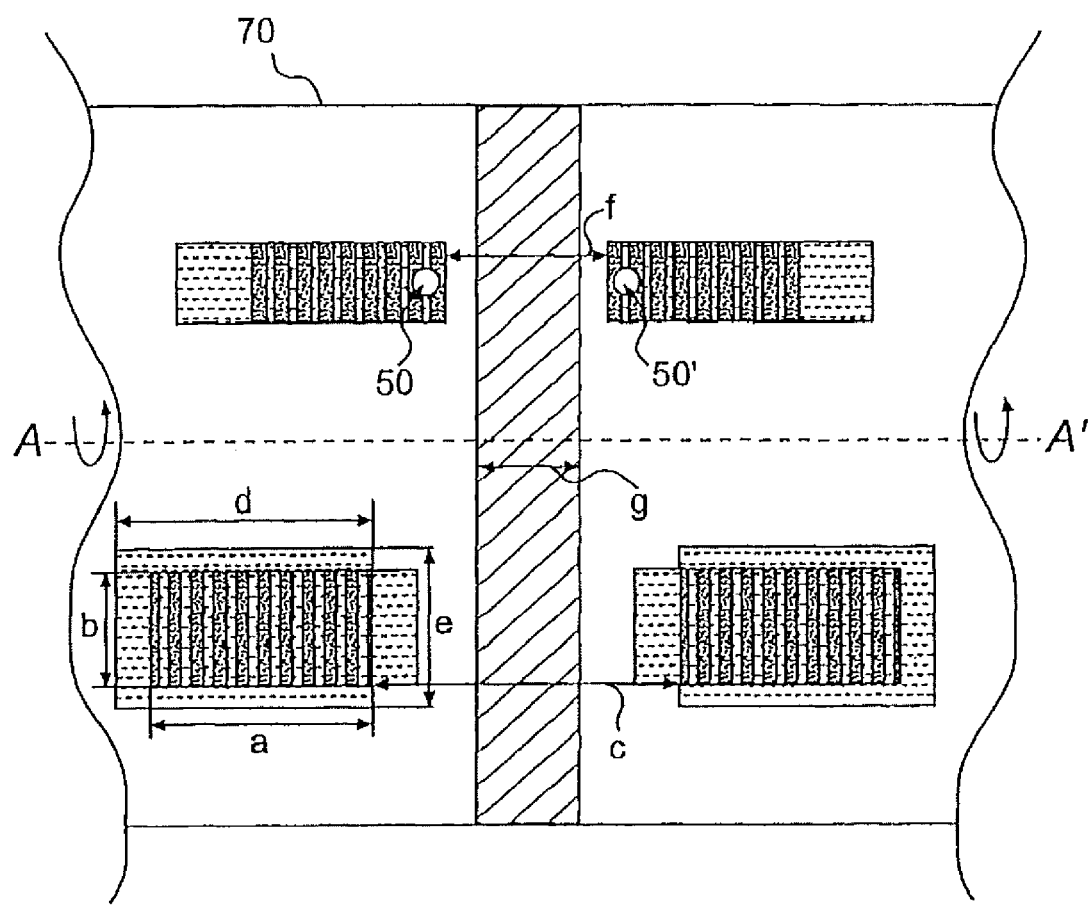
FIG. 6 is a schematic representation of a pair of textile-based electrodes and certain dimensions variable in their construction.

A portion of a wearable 110, fully integrated with two textile-based electrodes, is represented in FIG. 5. The wearable in FIG. 5 represents a sleeve, cuff, or band. In such an embodiment, the electrical device 200 is capable of receiving, storing, and/or transmitting certain biophysical parameters of a person or animal employing the wearable, fully integrated with textile-based electrodes.

As represented in FIG. 5, two textile-based electrodes can communicate directly with the electrical device 200, placed in a space formed between surfaces 72 and 74. The two conductive yarn portions 40 and 40' on the surface 78 are capable of contacting the skin of a wearer. As a result of skin contact with 40 and 40', any electrical signal originating from the wearer can be transmitted directly to 30 and 30' respectively, and, in turn, to electrical device 200, via the contacts 50 and 50'. Similarly, electrical device 200 may be capable of transmitting an electrical signal via contacts 50 and 50' and, in turn, through conductive yarns 30 and 30' and further in turn to conductive yarns 40 and 40', which contact the skin of the wearer and transmit the same signal to the wearer.

In another embodiment of the invention, the electrical device 200 is capable of biophysiological monitoring, such as sensing electrical signals associated with the electrical activity of the heart the wearer and thus the number of heart beats per unit time. The electrical device 200 can be engagable with contacts 50 and 50', as represented in FIG. 4, using conductive contacts 210 and 210'. The snap-engaged contacts 50 and 50' suitable for this application can be, for example, 19L and 21 L contacts, available from PRYM Consumer USA. Reinforcement fabrics can be provided under each snap 50, 50', for example, in the form of a woven piece of CORDURA®. These can serve to reduce the wear and eventual failure of the snaps located in the textile electrodes 30 and 30'.

The wearable 110 in FIG. 5 is in the form of a band that surrounds the mid-thorax of the wearer. The band can also be placed at other parts of the body, e.g. wrist, arm, waist, etc. The surface 78 of 110 is positioned toward the wearer's body and conductive yarn portions 40' and 40 are positioned horizontally so as to receive electrical signals associated with the electrical activity of a beating heart.

Optionally, the signal pickup from the wearer's skin may be further enabled using a portion of yarn, such as cotton yarn 46, 46' in FIG. 4, knitted into the fabric band portion surrounding 40 and 40'. Cotton yarns are known to be hydrophilic (as are, for example, silk, viscose, acetate and wool) and can promote the retention of body derived moisture in the vicinity of 40 and 40'.

It is also an option to provide a coating on or around the borders of the skin contacting electrodes 40 and 40', which helps promote sweating, thus allowing moisture to build up immediately after donning the wearable 110. Such coating may, for example, be desirable in applications where a wearer is not engaged in strenuous activity (in other applications, for example, where the wearer would be expected to be engaged in more strenuous activity, such coating may be less desirable). A suitable coating is, for example, ELASTOSIL R plus 573 electrically conductive silicone rubber (from Wacker Silicones, WACKER-CHEMIE GmbH, Germany).

Suitable electrical devices to demonstrate the function of the heart rate monitor embodiment include those made by POLAR Electro Oy, Professorintie 5, Finland, 90440 Kempele. The POLAR S810i™ and the POLAR RS800™ both include an electronics module (200 in the embodiment represented by FIG. 5) and a wrist worn device that communicates via radio frequency with the module. The wrist worn device logs the data of the wearer. Data can be obtained during the wearer's activities, including, for example, strenuous activity like running, cycling, or skiing.

This embodiment of the invention can be superior to other means to wear a device such as the POLAR SR800™ or the POLAR S810i™ By comparison, chest worn belts and straps known for use with the POLAR S810i™ are not as form fitting, comfortable, and unobtrusive. The provision of a garment, such as a knitted top or a sports bra, fully integrated for biophysiological monitoring, can lead to a superior performing wearable embodiment of the invention.

Examples of wearables that can incorporate textile-based electrodes according to embodiments of the present invention include any type of a garment, including any type of a sports or athletic garment. Specific examples of garments include shirts, tank tops, bras, and underwear. However, it is important to note that the wearable can also include bands, straps, belts, or any other form of wearable article. A one layer electrode patch 40 can also be cut/sewn onto any wearable article. Wearables can also be used in medical applications, such as for monitoring physiological parameters of patients.

Figure 7:
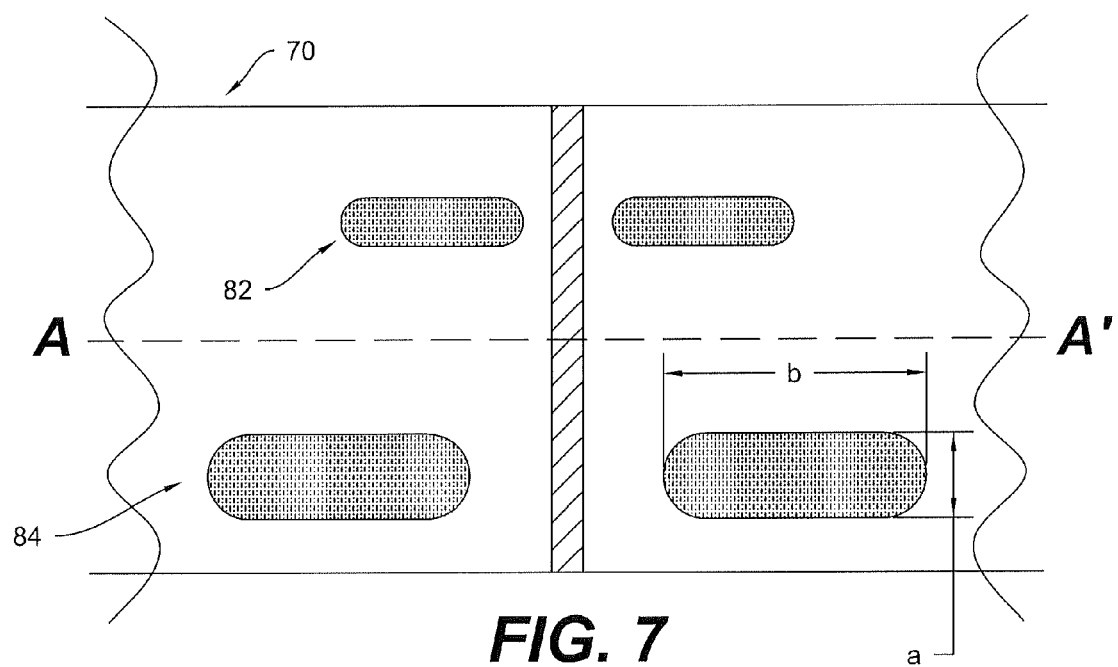
FIG. 7 is a schematic representation of pairs of textile-based electrodes with a first example of a graduated pattern.
Figure 8:
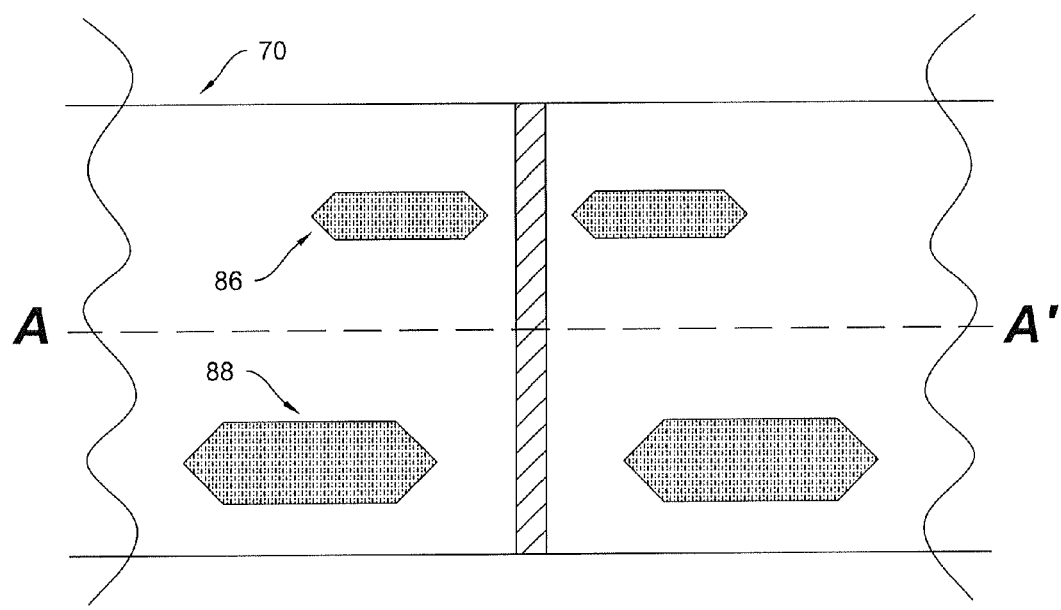
FIG. 8 is a schematic representation of pairs of textile-based electrodes with a second example of a graduated pattern.
Figure 9:
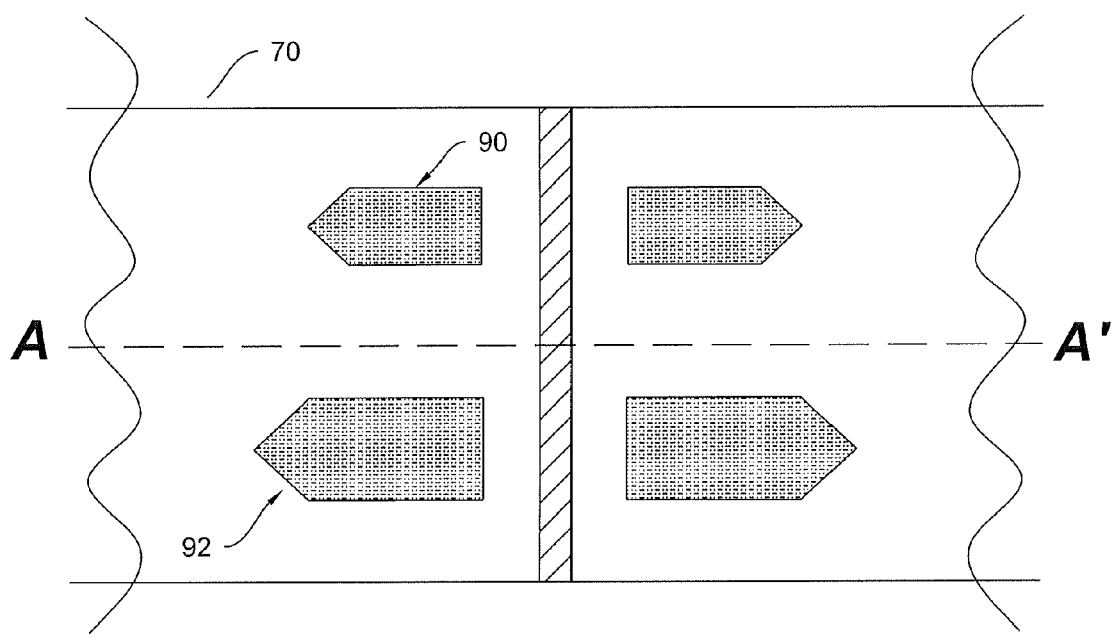
FIG. 9 is a schematic representation of pairs of textile-based electrodes with a third example of a graduated pattern.

FIGS. 7 to 17 show alternative textile-based electrodes with graduated patterns incorporated into a fabric portion 70. FIGS. 7 to 9 also show horizontal axis AA'. By folding along horizontal axis AA', a two-ply fabric portion may be formed. FIGS. 10 to 17 show the front view of two-ply fabric portion 70 with of textile-based electrodes with graduated patterns. These embodiments of textile-based electrodes with graduated patterns may also incorporate connection points 50 and 50' (not shown in FIGS. 7 to 17) for sending or receiving electrical signals.

In FIG. 7, the first electrodes 82 have an elongated oval periphery, in which the length is longer than the width. The second electrodes 84 have another elongated oval periphery, in which the length b is longer than the width a. By folding along horizontal axis AA', a two-ply fabric portion is formed.

These elongated oval graduated patterns 82, 84 may be formed by programming a circular knitting machine to pick up courses of electrically conductive yarn at different needle positions on the circular knitting machine. For example, the length of the first row in the graduated pattern is shorter than the length of the second row, and so on until the maximum length of the textile-electrode graduated pattern is reached at the apex portions of the oval. Then, the length of the next row may be shorter, and so on to complete the graduated pattern.

FIG. 8 shows alternative graduated patterns 86, 88 in which the peripheries of the textile-based electrodes are angled. The first electrodes 86 have an elongated hexagonal periphery, in which the length is longer than the width. The second electrodes 88 have another elongated hexagonal periphery, in which the length is longer than the width.

FIG. 9 shows alternative graduated patterns, 90, 92 in which the textile-based electrodes are angled at one end.

Figure 10:
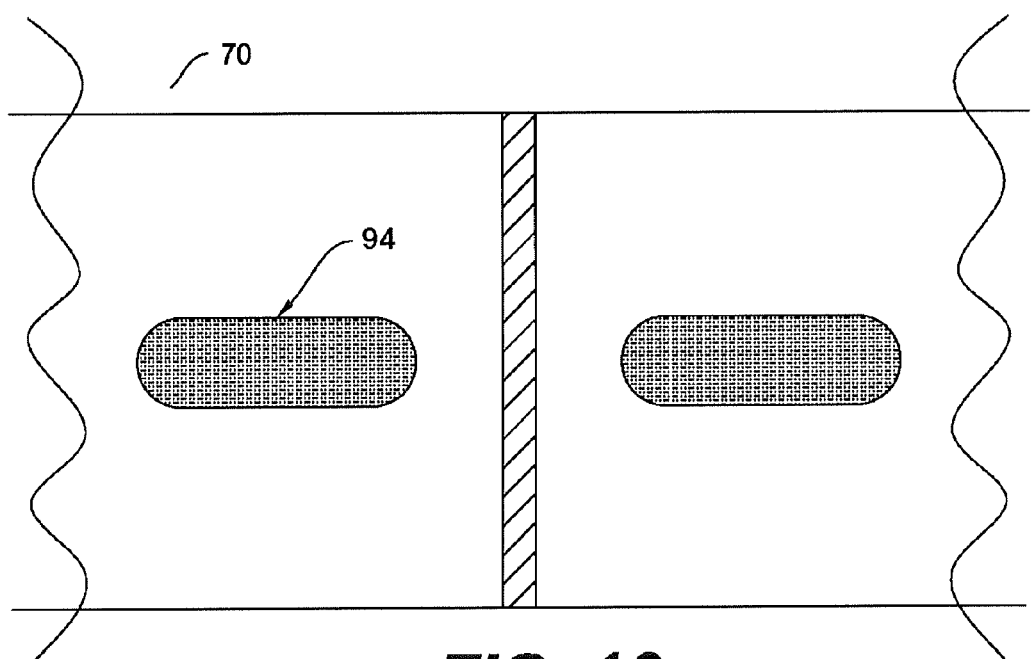
FIG. 10 is a schematic representation of a pair of textile-based electrodes with a fifth example of a graduated pattern.

FIG. 10 shows a pair of textile-based electrodes 94 where each electrode has a graduated pattern with an elongated oval periphery. Alternatively, such electrodes may be rounded on only one end.

Figure 11:
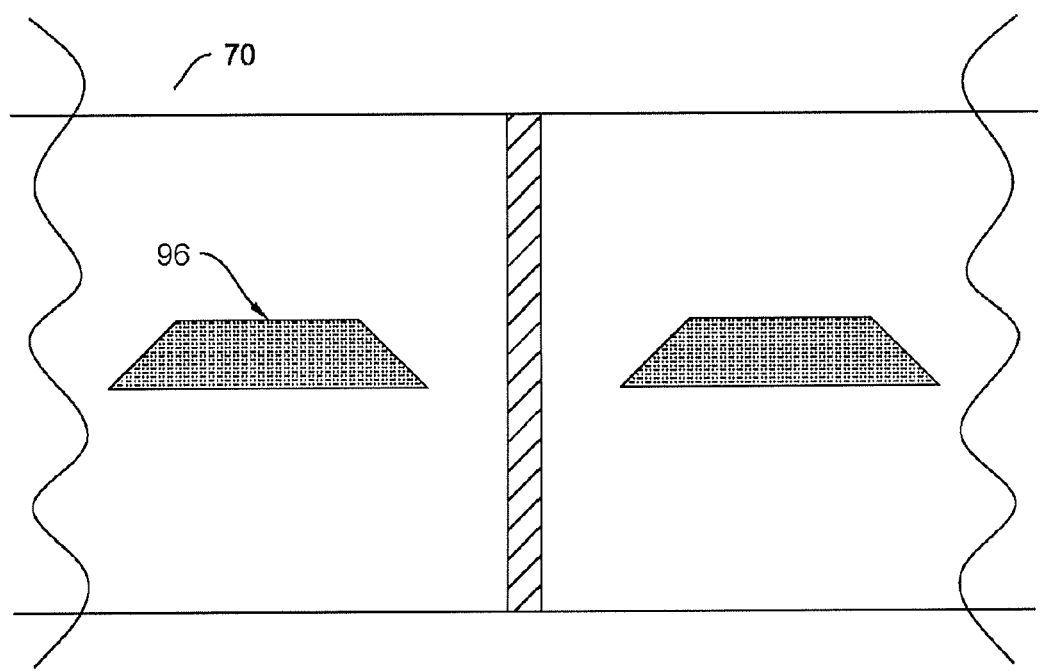
FIG. 11 is a schematic representation of a pair of textile-based electrodes with a sixth example of a graduated pattern.

FIG. 11 shows a pair of textile-based electrodes 96 where each electrode has a graduated pattern with slanted sides. The graduated pattern is shaped as a trapezoid, wherein the top row or course of electrically conductive yarn or fiber is knitted to a shorter length that the next row and so on, with the bottom row having the longest length in the graduated pattern.

Figure 12:
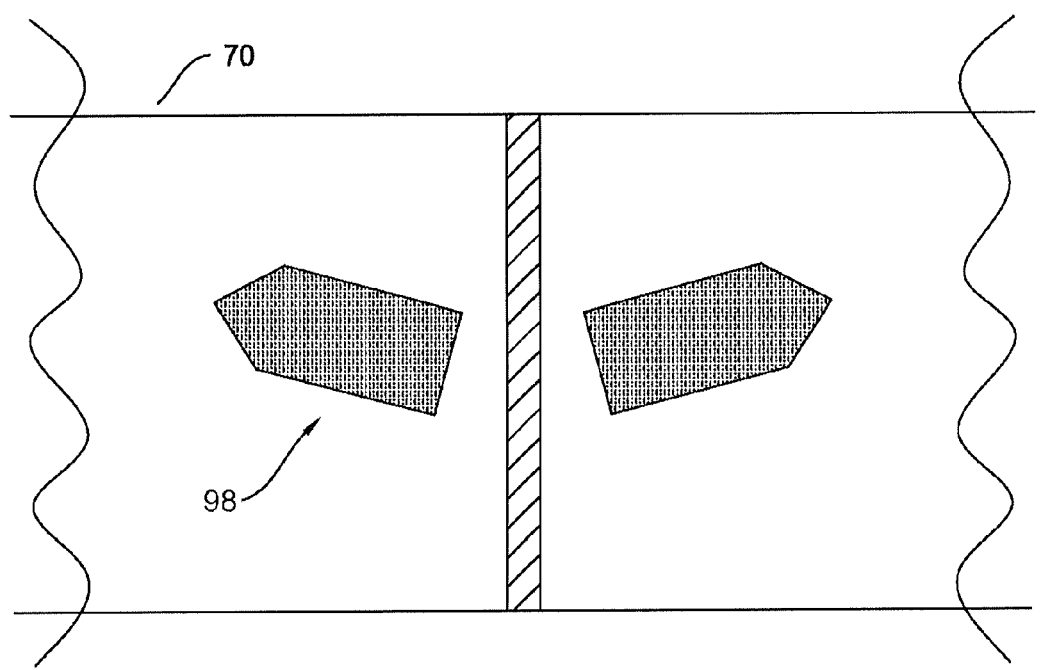
FIG. 12 is a schematic representation of a pair of textile-based electrodes with a seventh example of a graduated pattern.

FIG. 12 shows a pair of textile-based electrodes 98 where each electrode has a graduated pattern with angled ends. In this embodiment, the graduated pattern is an elongated pentagon. Here, each electrode is disposed within the fabric at an angle from a horizontal axis along the fabric portion in which the electrodes are formed.

Figure 13:
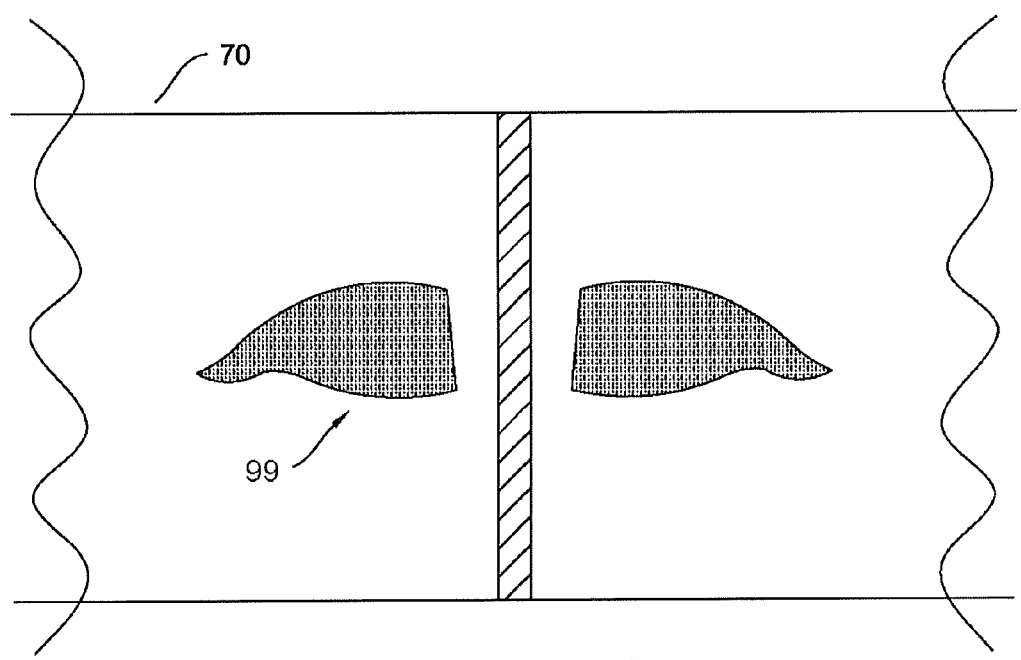
FIG. 13 is a schematic representation of a pair of textile-based electrodes with an eighth example of a graduated pattern.

FIG. 13 shows a pair of textile-based electrodes 99 where each electrode has a graduated pattern that has varying degrees of curvature on its top and bottom portions. As shown, the ends facing one another of the electrodes are straight, however, such ends alternatively may be formed in a curved or other alternative pattern. The straight ends facing one another of the electrodes are shown as slanted away, but also may be provided in parallel.

Figure 14:
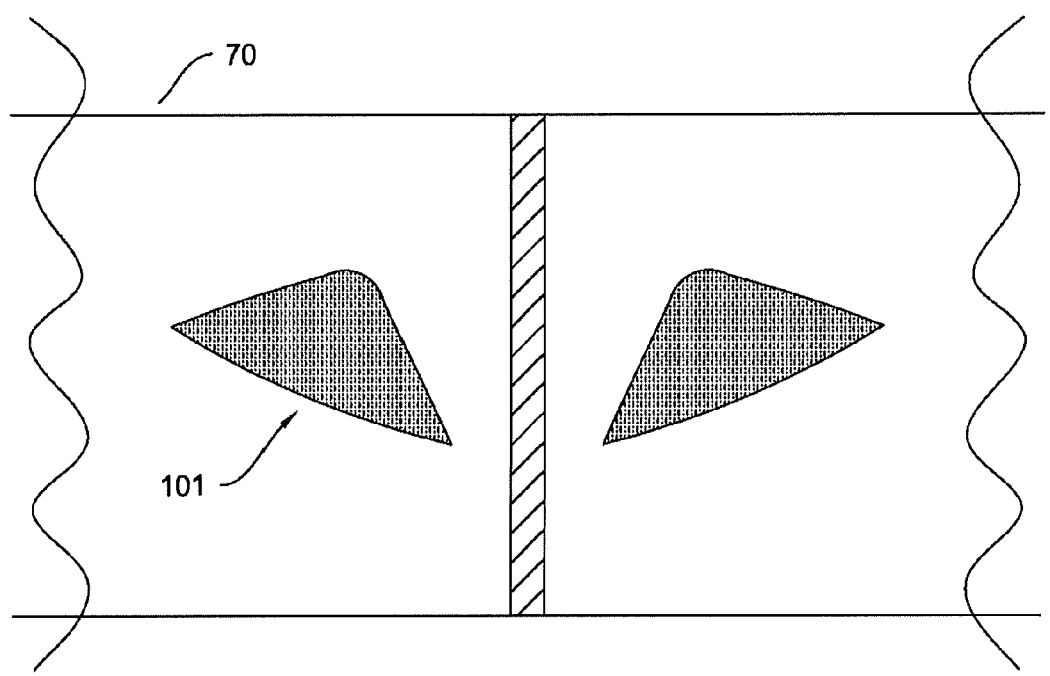
FIG. 14 is a schematic representation of a pair of textile-based electrodes with a ninth example of a graduated pattern.

FIG. 14 shows a pair of textile-based electrodes 101 where each electrode has a triangular-shaped graduated pattern. One apex of each triangular pattern is rounded. Each of the electrodes is disposed within the fabric at an angle from a horizontal axis along the fabric portion in which the electrodes are formed.

Figure 15:
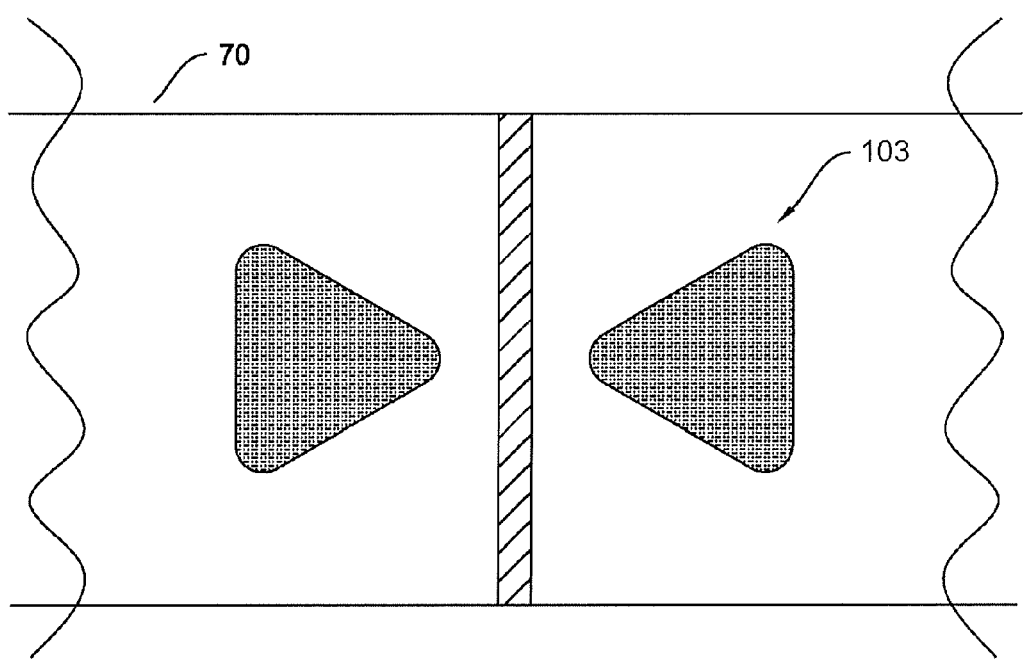
FIG. 15 is a schematic representation of a pair of textile-based electrodes with a tenth example of a graduated pattern.

FIG. 15 shows a pair of textile-based electrodes 103 where each electrode has a triangular-shaped graduated pattern. Each apex of the triangular pattern is rounded, and the electrodes are disposed in line with a horizontal axis along the fabric portion in which the electrodes are formed. Alternatively, the textile-based electrodes 102 may be disposed at angles to one another and/or to a horizontal axis along the fabric portion.

Figure 16:
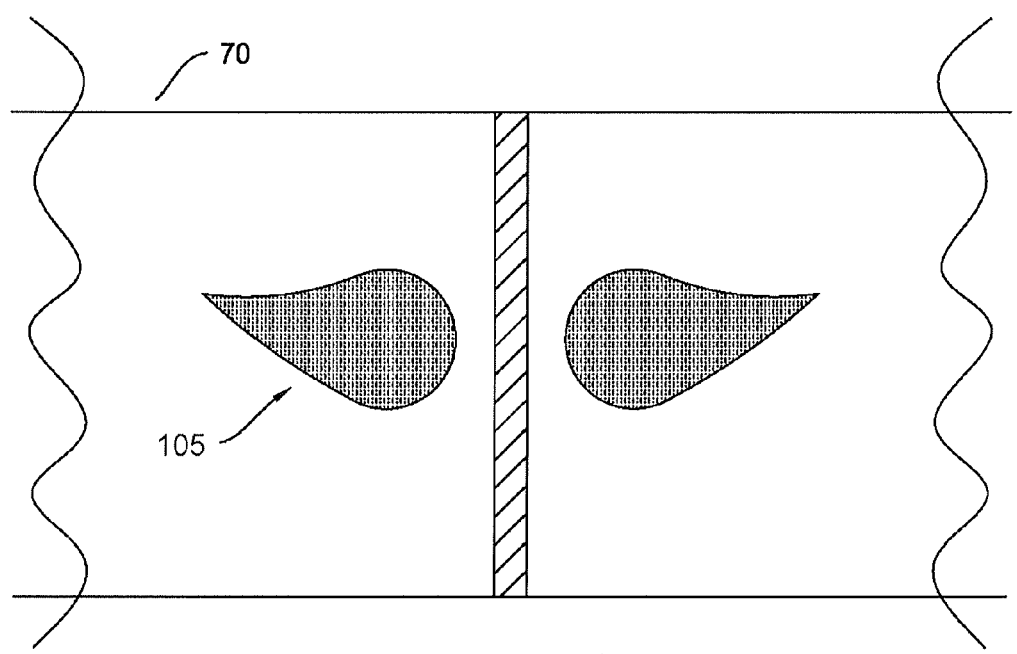
FIG. 16 is a schematic representation of a pair of textile-based electrodes with an eleventh example of a graduated pattern.

FIG. 16 shows a pair of textile-based electrodes 105 where each electrode has a tear-drop like graduated pattern. One end of the pattern is angled, while the other end is substantially circular or rounded.

Figure 17:
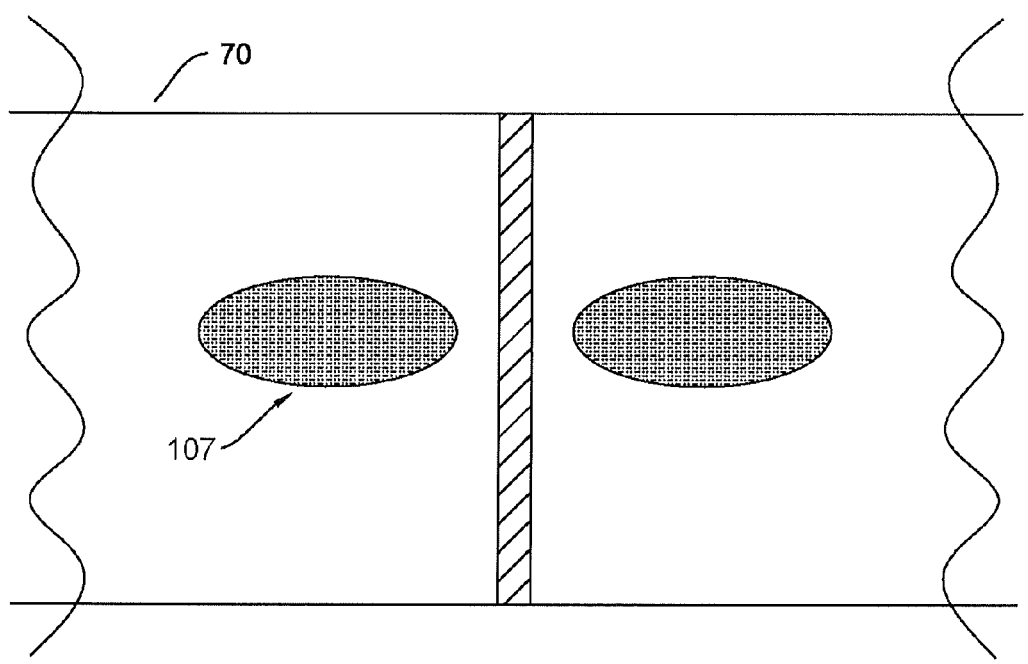
FIG. 17 is a schematic representation of a pair of textile-based electrodes with a twelfth example of a graduated pattern.

FIG. 17 shows a pair of textile-based electrodes 106 with an elliptical periphery. These elliptical graduated patterns may also be formed by programming a circular knitting machine to pick up courses of electrically conductive yarn at different needle positions on the circular knitting machine. For example, the length of the first row in the graduated pattern is shorter than the length of the second row, and so on until the maximum length of the textile-electrode graduated pattern is reached at the apex portions of the ellipse.

The alternative textile-based electrodes with graduated patterns, as shown in FIGS. 7 to 17, are formed by programming a circular knitting machine, as in those manufactured by SANTONI. To form the textile-based electrodes with graduated patterns, the circular knitting machines are programmed to pick up user specified needles/courses of electrically conductive yarn at different needle positions. The machines have one or more circular needle cylinders that have slots in their outer cylindrical surface. The slots are guides used by the needles as the needles travel to form stitch loops. The needles reciprocate between a maximum position and a minimum position into which they are moved by cams that act on the needle. During the operation of the machine, the cylinder and the needles are rotated. To produce textile-based electrodes with graduated patterns, some needles are required to produce stitch loops while others have to be moved to a different position to take up yarn without clearing the previous stitch. The machine is programmed to determine the required position and travel of each needle such that textile-based electrodes with graduated patterns can be incorporated into circularly knit garments.

TEST METHODS

Test methods for evaluating the efficacy of textile based electrodes are set forth in U.S. Pat. Nos. 7,308,294 and 7,474,910, the entire contents of which are incorporated by reference herein.

In order to test the suitability of embodiments falling within the scope of the present invention for use in biophysiological monitoring, the heart rates of several subjects were measured using Polar RS800™ and POLAR S810i™ electronics modules. The modules were mounted in an upper chest worn knit fabric band (i.e., 70) to compare the signal quality of monitoring belts using a control (a rectangular textile-sensor without a graduated pattern) against monitoring belts with variants of textile-sensors incorporating graduated patterns.

Examples were made in the form of heart rate monitoring belts or chest bands (listed as 1-6 in Table 1). The heart rate monitoring belts were made by circular knitting using a SMA-8-TOP1 seamless, 13 inch body size, knitting machine from SANTONI (hereinafter, "the SANTONI knitting machine"). In making the heart rate monitoring belts, a combination of different knitting constructions (including jersey and mock rib knit construction) using various types of yarns were used. In each example, the denoted electrode region was made using Xstatic® yarns of a silver metallized nylon yarn of 70 denier and 34 filaments from Laird Sauquoit Industries (Scranton, Pa., USA 18505) (hereinafter "X-static® 70/34").

In each of the heart rate monitoring belts of Examples 1-6, sensors of conductive yarn were knit into a base fabric. Two-ply 70 denier, 68 filament textured nylon from Unifi, Inc. was plated with Lycra® spandex (T-902C 260d). The nylon and Lycra® spandex were knitted together using the SANTONI knitting machine at a ratio of about 92% nylon and 8% Lycra® spandex (ratios of from about 75 to about 100% nylon and from 0 to about 25% Lycra® spandex are also possible), wherein both plain jersey stitching and mock rib (1×1, 3×1, 2×1, 2×2) stitching were used in the regions of the fabric containing the textile-based electrodes (the "conductive regions"), as well as the non-conductive regions of the fabric.

For the regions of the fabric containing the textile-based electrodes (or "conductive regions"), a conductive yarn was knitted on one side of the base fabric using the SANTONI knitting machine. The conductive yarn used in making heart rate monitoring belts of Examples 1-6 and the control was X-static® 70/34 (although composite yarns form Bekaert having approximately 80% polyester and 20% stainless steel could also be used). In this regard, conductive regions were knitted using plain jersey and mock rib stitch.

During indoor or outdoor exercise sessions lasting from 30-60 minutes, subjects wore monitoring belts that incorporated the control and the six variants. Indoor heart rate data was logged using proprietary Adidas® software. Outdoor heart rate data was logged according to the methods provided by POLAR with the S810i™ and the Polar RS800™ modules and wrist worn data logger.

In the heart rate monitoring belts of Examples 1-6, the dimensions of regions a×b (FIG. 7), varied, as shown in Table 1. Using these values, the area of each region was approximated and compared, in terms of percentage, against the control.

The quality of signal pick-up, during the start-up, middle and end of each exercise session was rated by a panel of experts. The presence of noise or other signal degradation was also noted. A score of 10 was considered excellent and a score of 1 was considered poor. An average rating was then calculated.

Table 1 provides a summary of the dimensions and average signal quality ratings for heart rate monitoring belts of Examples 1-6 and the control. The textile-based electrodes had the following periphery shapes:

Control: rectangular pattern with floats
Example 1: rectangular pattern without floats
Example 2: elongated oval pattern
Example 3: elongated oval pattern
Example 4: elliptical pattern
Example 5: elliptical pattern
Example 6: elliptical pattern

TABLE 1

| Example No. | Signal Quality Rating Start | Signal Quality Rating Middle | Signal Quality Rating End | Sensor Size Compared to Control | inside right sensor a (mm) | inside right sensor b (mm) | inside left sensor a (mm) | inside left sensor b (mm) |
|---|---|---|---|---|---|---|---|---|
| control | 8.7 | 8.8 | 8.5 | 100% | 29 | 78 | 29 | 78 |
| 1 | 8.3 | 8.1 | 6.0 | 76% | 22 | 78 | 22 | 78 |
| 2 | 7.3 | 8.6 | 9.1 | 57% | 16 | 47 | 30 | 51 |
| 3 | 7.6 | 9.0 | 8.4 | 33% | 16 | 47 | 16 | 47 |
| 4 | 8.1 | 8.1 | 7.2 | 27% | 17 | 36 | 17 | 36 |
| 5 | 9.1 | 6.4 | 7.6 | 27% | 17 | 36 | 17 | 36 |
| 6 | 7.2 | 9.1 | 8.7 | 29% | 17 | 36 | 17 | 36 |

Examples 1 to 6 demonstrate that textile-based electrodes with graduated patterns offer comparable signal quality to the control. As such, the textile-based electrodes with graduated patterns offer processing advantages in terms of knitting speed and needle wear without adverse impact on textile-based electrode performance in a wearable.

Nothing in this specification should be considered as limiting the scope of the present invention. All examples presented are representative and non-limiting. The above described embodiments of the invention may be modified or varied, and elements added or omitted, without departing from the invention, as appreciated by persons skilled in the art in light of the above teachings. It is therefore to be understood that the invention is to be measured by the scope of the claims, and may be practiced in alternative manners to those which have been specifically described in the specification.

What is claimed is:

1. A textile-based electrode, comprising:
a first fabric portion defining a fabric plane and comprising: (a) non-conductive yarns; and (b) at least one electrically conductive region in the fabric plane comprising electrically conductive yarn filaments, said region forming at least one graduated pattern having at least one graduated end that changes gradually or by degrees, the graduated pattern being formed from multiple knit courses of a circular knit in which a first course produces a first length and a second course produces a second length that is different from the first length.

2. The textile-based electrode according to claim 1, wherein the non-conductive yarns comprise one or more stretch-recovery yarns.

3. The textile-based electrode according to claim 1, wherein the electrically conductive yarn filaments comprise one or more stretch-recovery yarn filaments.

4. The textile-based electrode according to claim 1, wherein the electrically conductive region comprises a fabric having a textured or ribbed construction.

5. The textile-based electrode according to claim 1, wherein the electrically conductive region of the first fabric portion comprises at least one float yarn.

6. The textile-based electrode according to claim 1, wherein the electrically conductive region comprises an elastic yarn plated with a conductive yarn.

7. The textile-based electrode according to claim 1, wherein at least one hydrophobic material is incorporated into the electrically conductive region.

8. The textile-based electrode according to claim 1, wherein the electrically conductive region of the first fabric portion defines a length and a width and a thickness, and the length is longer than the width.

9. The textile-based electrode according to claim 1, wherein the graduated pattern has a shape selected from the group consisting of: rounded ends, angled ends, slanted ends, curved ends, and staggered ends.

10. The textile-based electrode according to claim 1, wherein the graduated pattern further comprises a third course that produces a third length that is different from the second length.

11. The textile-based electrode according to claim 1, further comprising a coating of polymer solution on and/or around the electrically conductive region of the first fabric portion.

12. A method for reducing needle wear when forming textile-based electrodes, comprising:
    programming a knitting machine to produce a fabric with at least one graduated pattern;
    forming the graduated pattern by knitting the fabric with electrically conductive yarns or fibers to form at least one electrically conductive region having the graduated pattern of multiple knit courses in which a first course produces a first length, a second course adjacent to the first course produces a second length that is different from the first length, and a third course adjacent to the second course produces a third length that is different from the second length; and
    knitting the fabric with nonconductive yarns or fibers to form nonconductive portions of the fabric.

13. The method for reducing needle wear of claim 12, wherein the knitting machine is a circular knitting machine.

14. The method for reducing needle wear of claim 12, wherein the at least one graduated pattern has ends selected from the group consisting of: rounded ends, slanted ends, curved ends, angled ends and staggered ends.

15. A textile-based electrode system, comprising:
    at least a first fabric portion and a second fabric portion; the first fabric portion comprising at least a first electrically conductive region with at least one first graduated pattern; the second fabric portion comprising at least a second electrically conductive region with at least one second graduated pattern that may be the same as or different from the at least one first graduated pattern; wherein the first and second fabric portions at least partially overlap one another; and wherein the electrically conductive region of the first fabric portion and the electrically conductive region of the second fabric portion are electrically coupled.

16. The textile-based electrode system according to claim 15, wherein at least one of: (i) the electrically conductive region of the first fabric portion and (ii) the electrically conductive region of the second fabric portion, comprises a float yarn.

17. The textile-based electrode system according to claim 15, wherein at least one of: (i) the electrically conductive region of the first fabric portion and (ii) the electrically conductive region of the second fabric portion, comprises at least a portion of an elastified electrically conductive yarn.

18. The textile-based electrode system according to claim 15, wherein at least one of: (i) the electrically conductive region of the first fabric portion and (ii) the electrically conductive region of the second fabric portion, comprises an elastic yarn at least partially plated with a conductive yarn.

19. The textile-based electrode system according to claim 15, wherein at least one of: (i) the electrically conductive region of the first fabric portion and (ii) the electrically conductive region of the second fabric portion, comprises a fabric having a textured or ribbed construction.

20. The textile-based electrode system according to claim 15, wherein: (i) the electrically conductive region of the first fabric portion and (ii) the electrically conductive region of the second fabric portion both comprise float yarns that are stitched together.

21. The textile-based electrode system according to claim 15, wherein the electrically conductive region of the first fabric portion and the electrically conductive region of the second fabric portion cooperate to provide a region of at least partial physical contact so as to electrically couple the first fabric portion and the second fabric portion.

22. A wearable article incorporating the textile-based electrode system of claim 15.

23. The wearable article of claim 22, comprising a garment selected from the group consisting of: brassiere, shirt, tank top, underwear, sleeve, cuff, strap, belt and band.

* * * * *